United States Patent [19]

Fiato et al.

[11] Patent Number: 4,537,867
[45] Date of Patent: Aug. 27, 1985

[54] PROMOTED IRON-COBALT SPINEL CATALYST FOR FISCHER-TROPSCH PROCESSES

[75] Inventors: Rocco A. Fiato, Scotch Plains; Stuart L. Soled, Madison; Angelo A. Montagna, Summit, all of N.J.

[73] Assignee: Exxon Research and Engineering Co., Florham Park, N.J.

[21] Appl. No.: 561,292

[22] Filed: Dec. 14, 1983

[51] Int. Cl.³ .............................................. B01J 23/78
[52] U.S. Cl. ........................................ 502/74; 502/84; 502/170; 502/174; 502/177; 502/178; 502/201; 502/207; 502/217; 502/218; 502/224; 502/226; 502/243; 502/250; 502/251; 502/252; 502/303; 502/304; 502/316; 502/324; 502/328; 502/330; 502/524
[58] Field of Search ................... 502/330, 524, 74, 84, 502/178, 207, 243, 250, 251, 252, 303, 304, 316, 324, 328, 177, 170, 174, 201, 217, 218, 224, 226; 518/717

[56] References Cited

U.S. PATENT DOCUMENTS

| | | | |
|---|---|---|---|
| 2,567,296 | 9/1951 | Milligan et al. | 502/330 |
| 2,662,090 | 12/1953 | Scharmann et al. | 260/449.6 |
| 2,686,195 | 8/1954 | McAdams et al. | 518/718 |
| 2,735,862 | 2/1956 | Buchmann et al. | 502/260 X |
| 2,850,515 | 9/1958 | Riblett | 260/449.6 |
| 4,154,751 | 5/1979 | McVicker et al. | 260/449.6 R |

FOREIGN PATENT DOCUMENTS 2050859A 1/1981 United Kingdom .

OTHER PUBLICATIONS

Stud. Surf. Catal. 7, PT/A, p. 432, (1981).
Kahn et al., "The Synthesis of Light Hydrocarbons From CO and Hydrogen Mixtures Over Selective Metal Catalysts", ACS 173rd Symposium, Fuel Div., New Orleans, (Mar. 1977), pp. 138–147.
"Mossbauer Spectroscopy of Supported Fe-Co Alloy Catalysts for Fischer-Tropsch Synthesis"–Journal of Catalysts, vol. 72, pp. 37–50, (1981).
"Mossbauer and Magnetic Studies of Bifunctional Medium-Pore Zeolite-Iron Catalysts Used in Synthesis Gas Conversion"–Advances in Chemistry Series, 1981, pp. 573–588, by Lo et al.
"Mossbauer Effect in Iron and Dilute Iron Based Alloys"–(Physics Reports, Section C of Physics Letters) 12, No. 5, (1974), pp. 335–374.
Gmelins Handbuch der Anorganische Chemie, vol. 8, Auflage (1959), pp. 408–413 and 1160–1161.
Hydrocarbon Processing, May 1983, pp. 88–96.
Chem-Ing.-Tech. 49, (1977), No. 6: pp. 463–468, (1977), by D. Kitzelmann et al., German.
C.R. Acad. Sc. Paris, p. 268, (May 28, 1969) by P. Courty and B. Delmon.
AIChE 1981 Summer National Meeting, Detroit, Preprint No. 408, (English).
Journal of Materials Science 7 (1972), pp. 1383–1390, by A. C. C. Tseung, and J. R. Goldstein.
ACS Meeting, Division of Petroleum Chemistry, Mar. 1978, entitled "Catalytic Synthesis of Light Olefinic Hydrocarbons from CO and Hydrogen Over Some Iron Catalysts", by C. H. Yang and A. G. Oblad.
Journal of Catalysis 32, pp. 452–465, (1974), by J. R. Goldstein et al.
J. Phys. Chem. Solids, 1959, vol. 9, pp. 165–175, by G. H. Jonker.
"The Fischer-Tropsch and Related Synthesis", by Storch, Golombic and Anderson, (Wiley), pp. 242–243.
Catal. Rev.-Syn. Eng. 21 (2), pp. 225–274, (1980).
J. Phys. Chem. Solids, 1976, vol. 37, pp. 619–624, by P. J. Murray and J. W. Linnett.
"Numerical Data and Functional Relationships in Science and Technology", Landolt–Bornstein, New Series, vol. 12, part B, Magnetic and Other Properties of Oxides and Related Compounds: Spinels, Iron Oxides and Iron-Metal-Oxygen Compounds, editor K. H. Hellwege, pp. 245–250.
Kirk-Othmer, "Encyclopedia Of Chemical Technology", 3rd Edition, vol. 13, pp. 90–95.
Journal of Catalysis, vol. 72, pp. 95–110, (1981), by J. A. Amelse, L. A. Schwartz and J. B. Butt.
Hydrocarbon Processing, Nov. 1980, pp. 139–142, "Make Olefins From Syn Gas", by V. U. S. Rao and R. J. Gormley.
Z. Physik Chemie Neue Folge 112, 215–233, (1978), by Kitzelman et al., "In Situ Study of the Primary Reactions in the Hydrogenation of CO on Iron Catalysts", J.C.S. Chem. Comm., pp. 428–430, (1983).

Primary Examiner—W. J. Shine
Attorney, Agent, or Firm—R. J. North; Edward M. Corcoran

[57] ABSTRACT

Iron-cobalt spinels which contain low levels of cobalt, in an iron/cobalt atomic ratio of 7:1 to 35:1, are converted to Fischer-Tropsch catalysts upon reduction and carbiding that exhibit high activity and selectivity to $C_2$—$C_6$ olefins and low $CH_4$ production.

19 Claims, No Drawings

PROMOTED IRON-COBALT SPINEL CATALYST FOR FISCHER-TROPSCH PROCESSES

FIELD OF THE INVENTION

This invention relates to a Fischer-Tropsch process for producing low molecular weight olefins, particularly those in the $C_2$–$C_4$ range, using as a catalyst, an unsupported alkali or alkaline earth metal salt promoted iron-cobalt single phase spinel, in which the atomic ratio of Fe:Co is 7:1 or above, and said spinel having a measured BET nitrogen surface area of up to about 5 $m^2/g$.

DISCLOSURES IN THE ART

Fischer-Tropsch processes have long been known to produce gaseous and liquid hydrocarbons containing $C_2$–$C_4$ olefins. Because of the importance of $C_2$–$C_4$ olefins, particularly as feedstocks for the chemical industry, modifications of the Fischer-Tropsch process are constantly being pursued toward the goals of maximizing $C_2$–$C_4$ olefin selectivity with the particular objective of maintaining high catalyst activity and stability under the reaction conditions. The main thrust of the efforts in this area has been in the area of catalyst formulation.

Coprecipitated iron-based catalysts, including those containing cobalt, are known for producing $C_2$–$C_4$ olefins. High levels of cobalt in an iron-cobalt alloy are known to produce enhanced selectivity to olefinic products, as described in *Stud. Surf. Sci. Catal.* 7, Pt/A, pp. 432 (1981).

Other disclosures in the art directed to coprecipitated iron-cobalt catalysts and/or alloys include: U.S. Pat. No. 2,850,515, U.S. Pat. No. 2,686,195, U.S. Pat. No. 2,662,090, and U.S. Pat. No. 2,735,862; AICHE 1981 Summer Nat'l Meeting Preprint No. 408, "The Synthesis of Light Hydrocarbons from CO and $H_2$ Mixtures over Selected Metal Catalysts" ACS 173rd Symposium, Fuel Division, New Orleans, Mar. 1977; J. Catalysis 1981, No. 72(1), pp. 37–50; Adv. Chem. Ser. 1981, 194, 573–88; Physics Reports (Section C of Physics Letters) 12 No. 5 (1974) pp. 335–374; UK Patent Application No. 2050859A; J. Catalysis 72, 95–110 (1981); Gmelins Handbuch der Anorganische Chemie 8, Auflage (1959), pp. 59; Hydrocarbon Processing, May 1983, pp. 88–96; and Chem. Ing. Tech. 49 (1977) No. 6, pp. 463–468.

There is further disclosed a method for producing high surface area metal oxides in the French article, "C. R. Acad. Sc. Paris", p268 (May 28, 1969) by P. Courte and B. Delmon. The article describes a process for producing high surface area metal oxides by evaporating to dryness aqueous solutions of the corresponding glycolic acid, lactic acid, malic or tartaric acid metal salts. One oxide that was prepared by their described method was $CoFe_2O_4$.

However, the above references do not describe or suggest the use of single phase iron-cobalt spinels having an Fe:Co atomic ratio of 7:1 or above or suggest their applicability in conducting or carrying out Fischer-Tropsch processes for synthesizing $C_2$–$C_4$ olefins.

What is particularly desired in fixed bed Fischer-Tropsch processes are new catalysts for selectively producing high levels of $C_2$–$C_4$ olefins and low levels of methane under the desirable combined conditions of high catalyst activity and stability.

SUMMARY OF THE INVENTION

It has been found that unsupported alkali or alkaline earth metal salt promoted iron-cobalt single phase spinels containing low levels of cobalt, i.e. iron:cobalt atomic ratios of 7:1–35:1 and higher provide desirable catalyst properties in fixed bed Fischer-Tropsch processes. The initial spinels are single phase and isostructural with $Fe_3O_4$ as shown by X-ray diffractometry and possess measured BET nitrogen surface areas of up to 5 $m^2/g$ (square meters per gram).

The spinels are prepared in a high temperature solid state sintering reaction in a temperature range of about 600° to 1100° C. between stoichiometric amounts of mixtures of the component metal oxides and/or metals, in an inert or vacuum atmosphere. The spinels prepared in this manner are then treated with promoter agents, alkali metal and alkaline earth metal salts, and particularly potassium carbonate. The resulting combined iron and cobalt/potassium atomic ratio is desirably in the range of about 20:1 to 200:1. The promoted catalyst is then reduced in a hydrogen containing gas and carbided before use in the Fischer-Tropsch process.

In accordance with this invention there is provided a hydrocarbon synthesis catalyst composition comprising an unsupported, Group IA or IIA metal salt promoted iron-cobalt single phase spinel, said spinel having the initial empirical formula:

$$Fe_xCo_yO_4$$

wherein x and y are integer or decimal values, other than zero, with the proviso that the sum of x+y is 3 and the ratio of x/y is 7:1 or above, said spinel exhibiting a powder x-ray diffraction pattern substantially isostructural with $Fe_3O_4$ and said spinel having an initial BET surface area of up to about 5 $m^2/g$.

Preferred embodiments of the composition include the substantially reduced and carbided form of the spinel, which is an active Fischer-Tropsch catalyst in fixed bed process for producing low molecular weight olefins.

Furthermore, there is provided a process for producing the subject spinel portion of the composition comprising the step of heating a mixture of cobalt and iron, as their oxides, free metals, or mixtures thereof, to produce the empirical composition: $Fe_xCo_yO_4$, where x and y are integers or decimal values, other than zero, and where the sum of x+y is 3, and the ratio of x/y is about 7:1, or above, for a time sufficient to produce said single phase spinel being isostructural with $Fe_3O_4$, and having a surface area of up to about 5 $m^2/g$.

There is further provided a process for synthesizing a hydrocarbon mixture containing $C_2$–$C_6$ olefins comprising the step of contacting a catalyst composition, comprised of an unsupported Group IA or IIA metal salt promoted iron cobalt spinel, said spinel initially exhibiting a single spinel phase, being isostructural with $Fe_3O_4$, as determined by X-ray diffractometry, and possessing an initial BET nitrogen surface area of up to about 5 $m^2/g$, and an iron-cobalt atomic ratio of 7:1 or above, with a mixture of CO and hydrogen under process conditions of pressure, space velocity and elevated temperature for a time sufficient to produce said $C_2$–$C_6$ olefins.

DESCRIPTION OF THE INVENTION AND PREFERRED EMBODIMENTS

The subject iron-cobalt spinels are new compositions of matter which are isostructural with $Fe_3O_4$, as determined by x-ray diffractometry using copper K alpha radiation and exhibit a single spinel phase. By the term "spinel" is meant a crystal structure whose general stoichiometry corresponds to $AB_2O_4$, where A and B can be the same or different cations. Included within this definition is the commonly found spinel $MgAl_2O_4$. A and B can have the following cationic charge combinations: A=+2, B=+3, A=+4, B=+2, or A=+6, B=+1. Spinels are arranged of an approximately cubic close-packed arrangement of oxygen atoms with $\frac{1}{8}$th of the available tetrahedral interstices and $\frac{1}{2}$ of the octahedral interstices filled, and can exhibit hundreds of different phases. Further description of the spinel structure can be found in "Structural Inorganic Chemistry" by A. F. Wells, Third Edition, Oxford Press, and the article "Crystal Chemistry and Some Magnetic Properties of Mixed Metal Oxides With the Spinel Structure" by G. Blasse, Phillips Research Review Supplement, Volume 3, pp 1–30 (1964). By the term "isostructural" is meant crystallizing in the same general structure type in that the arrangement of the atoms remains very similar with only minor changes in unit cell constants, bond energies and angles. By the term "single phase spinel", as used herein, is meant one structural and compositional formula, corresponding to a single spinel material into which all of the metal components are incorporated, and exhibiting one characteristic X-ray diffraction pattern.

The subject iron-cobalt spinel possesses a BET surface area up to about 5 $m^2/g$, as determined by the well-known nitrogen gas BET surface area measurement technique as described in the reference JACS 60, p. 309 (1938) by S. Brunauer, P. H. Emmett, and E. Teller. Generally, the spinel has a surface area of about 0.1 to 1 $m^2/g$. This range of surface area generally corresponds to a particle size range of about 1 to 10 microns.

The iron to cobalt atomic ratio of the metals in the spinel is about 7:1 or above and is preferably in the range of about 7:1 to 35:1.

The spinel can be represented by the formula: $Fe_xCo_yO_4$, wherein x and y are decimal or integer values, other than zero, and wherein the sum of x plus y is 3, and the ratio of x to y is 7:1 or above and preferably being about 7:1 to 35:1. Particularly preferred is where the iron to cobalt atomic ratio is about 19 to 20:1. The spinel may comprise a mixture of spinels of different iron-cobalt atomic ratios, being in admixture.

Representative examples of the various spinels corresponding to the formula are $Fe_{2.85}Co_{0.15}O_4$, $Fe_{2.625}Co_{0.375}O_4$, $Fe_{2.97}Co_{0.03}O_4$ and $Fe_{2.25}Co_{0.75}O_4$.

Physical properties in general of these subject spinels are similar to those of magnetite, $Fe_3O_4$, and include: melting point of above 1400° C., and color of brownish to blackish.

The iron-cobalt spiels are used in unsupported form in $H_2$/CO hydrocarbon synthesis.

A promoter agent is also used in the composition and is used to particularly promote olefin formation in the process. Representative examples of classes of suitable promoter agents include hydroxides of Group IA and Group IIA metals, alkali metal and alkaline earth metal salts including carbonates, bicarbonates, organic acid salts i.e., acetates, inorganic acid salts, i.e. nitrate, halide, and sulfate salts of Group IA and IIA metals including lithium, sodium, potassium, cesium, rubidium, barium, strontium, magnesium, and the like. Preferably, the promoter agent is deposited or impregnated substantially on the surface of said spinel composition.

Representative examples of specific promoter agents are potassium carbonate, potassium sulfate, potassium bicarbonate, cesium chloride, rubidium nitrate, lithium acetate, potassium hydroxide, and the like. Preferred are the Group IA compounds and a particularly preferred promoter agent is potassium carbonate. The promoter, if used, is generally present in about a 0.1 to 10 gram-atom % as the metal ion of the total combined metal gram-atoms present. A preferred level of promoter agent is in the range of 1 to 2 gram-atom % of the total combined metal graom-atoms present. In the empirical formulas used herein, the amount of the promoter agent, e.g., potassium, is expressed in terms of gram atom percent based on the total gram-atoms of metals used. Thus, "1 gram-atom of potassium" signifies the presence of 1 gram-atom of potassium per 100 total gram atoms of combined gram atoms of Fe and Co. Thus, the symbol "1%K" as used herein indicates 1 gram-atom percent potassium based on each 100 gram atoms of the total combined gram atoms of iron and cobalt present.

A particularly preferred spinel composition of the subject invention is $Fe_{2.85}Co_{0.15}O_4$/1%K (potassium taken as the carbonate).

The catalyst spinel in the subject process may also be used in conjunction and admixture with a diluent material; one which aids in heat transfer and removal from the catalyst bed. Suitable materials include powdered quartz, silicon carbide, powdered borosilicate glass, $SiO_2$, porous silica, kieselguhr, zeolites, talc, clays, Group II to VII metal oxides and rare earth oxides including $TiO_2$, $SiO_2$, $Al_2O_3$, MgO, $La_2O_3$, $CeO_2$, $Cr_2O_3$, $MnO_2$, and the like. Preferred is powdered quartz.

The diluent, if used, is generally used in a 1:4 to 9:1 diluent/spinel catalyst composition weight ratio. Preferred is a 1:1 weight ratio.

The utility of these spinels is their ability upon subsequent reduction and carbiding to form active catalysts in a fixed bed Fisher-Tropsch process for making $C_2$–$C_4$ olefins from CO/hydrogen.

The reduced and carbided forms of the above-described spinel are also subjects of this invention.

The subject spinel is prepared by a solid state high temperature reaction between (1) the component oxides, i.e. $Fe_3O_4$ and $Co_3O_4$, or (2) a mixture of iron metal, cobalt oxide and iron oxide, i.e. Fe metal, $Co_3O_4$ and $Fe_2O_3$, or (3) a mixture of cobalt metal, iron oxides and cobalt oxide, i.e. Co, $Fe_3O_4$, $Fe_2O_3$ and $Co_3O_4$ or (4) a mixture of iron and cobalt metals, iron oxide and cobalt oxide, i.e. Fe, Co, $Fe_2O_3$ and $Co_3O_4$, in the correct stoichiometric metals and oxygen ratio to result in the empirical formula for the composition as given above. Preferred is indicated reaction (1) between iron oxide and cobalt oxide. The reaction is conducted at temperatures in the range of about 600° to 1100° C. and preferably from about 800 to 900° C., in an inert gas, oxygen-free atmosphere, or vacuum environment. Examples of useful inert gases are helium, nitrogen, argon, and the like. The solid state high temperature reaction "sintering" should be performed on thoroughly mixed samples of the metal oxides and/or metal oxide mixtures. A method of forming the mixture is by intimate grinding and shaking. The sintering reaction should be conducted until a powder X-ray diffraction pattern indicates a single spinel phase is formed, being isostructural with $Fe_3O_4$, which generally requires about an 8 to 24 hour period and preferably about a 12 to 18 hour period. Generally, at the end of each reaction period the material is thoroughly ground and mixed and then resubjected to the high temperatue conditions for an additional 1 to 5 cycles or until powder x-ray diffraction reveals the presence of a single spinel phase.

Prior to the hydrocarbon synthesis run, the iron-cobalt spinel is reduced in a reducing atmosphere at elevated temperature, generally in a temperature range of about 200° to 500° C. and preferably 350° to 450° C. The reduction can be carried out with various reducing gases including hydrogen, CO, and mixtures thereof, and the like. Preferably, hydrogen gas, either by itself or in an inert carrier medium such as helium, neon, argon, or nitrogen, is preferably used. The pressure of the reducing gas in this procedure may be in the range of 1.5 to 1000 psig and preferably in the range of 15 to 150 psig. The reducing gas feed rate may be in the range of 1–10,000 V/V/hr and preferably in the range of 10–1000 V/V/hr. The reduction is carried out until the resulting Fe—CO alloy is substantially reduced and exhibits a powder X-ray diffraction pattern isostructural with alpha iron. This reduction usually requires about 2–20 hours.

The resulting reduced spinel generally has a BET surface area of up to 3 $m^2/g$ and is useful in forming a carbided iron-cobalt catalyst useful in the subject Fischer-Tropsch process for making $C_2$ to $C_6$ olefins as described herein.

The iron-cobalt catalyst which is believed to be the primary active catalyst in the process can be produced by carbiding the reduced iron-cobalt spinel, described hereinabove, generally having an X-ray diffraction pattern isostructural with chi $Fe_5C_2$ (Hagg carbide), by heating at elevated temperature in a suitable carbiding atmosphere, containing CO, $H_2/CO$, and mixtures thereof. The spinel can also be reduced and carbided, concurrently, by contact with a $CO/H_2$ atmosphere under the hydrocarbon synthesis conditions described below.

Also a subject of the instant invention is a Fischer-Tropsch fixed bed process for producing $C_2$–$C_6$ olefins by utilizing the reduced and carbided iron-cobalt spinel, described hereinabove.

Although a fixed bed Fischer-Tropsch process is one desired mode for utilizing the claimed catalysts described herein, a slurry type process wherein the catalyst is suspended in a liquid hydrocarbon can also be utilized, as described in copending application, U.S. Ser. No. 561,192, filed Dec. 14, 1983, hereby incorporated by reference for that purpose.

The subject fixed bed process utilizes the above-described materials, as catalyst or catalyst precursors: the iron-cobalt spinel, or a mixture of iron-cobalt spinels, of different iron-cobalt atomic ratios, being in admixture with, isostructural with $Fe_3O_4$, and its reduced and carbided form. The reduced and carbided materials are generally made in situ in the apparatus, prior to, and during, the carrying out of the hydrocarbon synthesis process. A full discussion of the spinel and reduced form materials, their properties and their preparation are given hereinabove and need not be reiterated.

Prior to the CO/hydrogen hydrocarbon synthesis fixed bed run, the iron-cobalt spinel is generally conditioned in the apparatus by purging with nitrogen to remove reactive gases and then the temperature is increased to the reaction temperature range. Then the system is generally subjected to the above-described hydrogen treatment for a sufficient time to insure complete reduction of metal oxides. However, the pressure, space velocity, and temperature during this reduction step are not critical and can be utilized in the range which is actually used during actual hydrocarbon synthesis.

Following the reduction step, the CO/hydrogen feedstream is introduced into the apparatus catalyst chamber and the pressure, space velocity, temperature, and hydrogen/CO molar ratio are then adjusted as desired, for hydrocarbon synthesis conditions. Optionally, the reduction/carbiding can be carried out concurrently by contact with the $CO/H_2$ mixture at elevated temperature.

In the process, the hydrogen and CO are used in a molar ratio in the gaseous feedstream of preferably about a 0.5 to 2.5 molar $H_2/CO$ ratio and more preferably 1:1 to 2:1 molar ratio. Higher and lower molar ratios may also be used.

The temperature in the process is generally in the region of about 200° to 350° C. and preferably being 250° to 300° C. Higher temperatures in the range 300°–350° C. tend to promote higher % CO conversion, lighter products, more methane and more $CO_2$, formed from the water-gas shift reaction.

The pressure useful in the process is generally conducted in the range of about 50 to 1000 psig and preferably about 100 to 300 psig. Higher and lower pressures can also be used.

The space velocity, used in the process is expressed as "standard" hourly space velocity (SHSV) and is generally about 200 to 4000 volumes of gaseous feedstream/per volume of dry catalyst (excluding diluent)/per hour and is preferably in the range of about 400 to 1200 V/V/hr. Higher and lower space velocities can also be used where higher space velocities tend to lead to increased olefin contents but decreased % CO conversion.

The percent CO conversion obtainable in the subject process while providing substantial quantities of $C_2$–$C_6$ olefins, ranges from about 20 to 98% and preferably above about 30%. Higher and lower ratio percentages of CO conversion may also be utilized. "Total hydrocarbons" produced in the process is related to the selectivity of percent CO conversion to hydrocarbons, being hydrocarbons from $C_1$ to about $C_{40}$ and above inclusive, and is generally about 0 to 50 percent, and higher, of the total CO converted and the remainder being substantially converted to $CO_2$.

The percent total $C_2$–$C_6$ hydrocarbons of the total hydrocarbons produced, including olefins and paraffins is generally about 20 to 80 wt. % and preferably about 50 to 80 wt. %. The percent of $C_2$–$C_6$ olefins produced of the $C_2$–$C_6$ total hydrocarbons produced is generally about 50 to 90 wt. % and preferably about 70 to 90 wt. % of the $C_2$–$C_6$ total hydrocarbons. The olefins produced in the process are substantially alpha olefins.

The selectivity to methane based on the amount of CO conversion is about 2 to 12 weight percent of total hydrocarbons produced. Preferably about 10 percent and lower methane is produced in the process.

As discussed above, the percent selectivity to $CO_2$ formation in the process is in the range of about 10 to 50 percent of CO converted, and generally about 30 to 50 percent.

The reaction process variables are preferably adjusted to minimize $CO_2$ production, minimize methane production, maximize percent CO conversion, and maximize percent $C_2$-$C_6$ olefin selectivity, while achieving activity maintenance in the catalyst system.

The catalyst in the process may become contaminated with high molecular weight hydrocarbons on exposure to carbon monoxide hydrogenation reaction conditions. As a result of this catalyst activity may be diminished. In the event that this is observed it may be possible to recover nearly full catalyst activity by exposing the catalyst to a solvent wash and/or hydrogen treatment at elevated temperatures. We have found that this procedure can in some cases restore the catalyst with its initial performance characteristics.

Generally, this format can be achieved in a preferred mode of operating the process where the formula of the catalyst used in $Fe_{2.85}Co_{0.15}O_4/1\%K$, having about 1 $m^2/g$ BET surface area. The pretreatment procedure is conducted at 500° C. in a 9:1 $H_2/N_2$ stream @ 680 v/v/hr. under 100 psig for 5–7 hours, and the hydrocarbon synthesis run is conducted at the CO/hydrogen molar ratio is 1:1 to 2:1, the temperature is conducted in the range 230°–270° C., at a pressure of 150–300 psig, and space velocity 1000–1800 v/v/hr (SHSV). By carrying out the above process in the stated variable ranges efficient activity maintenance and production of $C_2$-$C_6$ olefins an be achieved.

The effluent gases in the process exiting from the reactor may be recycled if desired to the reactor for further CO/hydrocarbon synthesis.

Methods for collecting the products in the process are known in the art and include distillation, fractional distillation, and the like. Methods for analyzing the product liquid hydrocarbons and gaseous streams are also known in the art and generally include gas chromatography, liquid chromatography, high pressure liquid chromatography and the like.

Apparatus useful in the preferred process is any conventional fixed bed type reactor, being horizontal or vertical, moving bed, fluid bed, and the like. Other apparatus not specifically described herein will be obvious to one skilled in the art from a reading of this disclosure.

The following examples are illustration of the best mode of carrying out the claimed invention as contemplated by us and should not be construed as being limitations on the scope and spirit of the instant invention.

EXAMPLE 1

Solid solutions with the generic empirical formula: $Fe_{3-y}Co_yO_4/1\%K$ (1 gram-atom percent potassium as the carbonate) were prepared by the following procedure. Mixtures of $Fe_2O_3$, Fe metal and $Co_3O_4$ in the following molar ratios, $(4/3 - 4y/9)$ $Fe_2O_3 + \frac{1}{3}$ $(1-y/3)$ $Fe + y/3$ $Co_3O_4$, where the value of y independently was: 0, 0.03; 0.150; 0.375; and 0.750, corresponding respectively to the following weights in grams of $Fe_2O_3$, Fe metal, and $Co_3O_4$; 21.080, 1.8400, 0.00; 22,750, 1.9891, 0.2594; 21.797, 1.9054, 1.2974; 20.0163, 1.7502, 3.2338; 11.381, 0.95090, 4.2904. The materials (reagent quality or better from Alfa Chemicals Co.) were well mixed, placed into a quartz tube, evacuated to $10^{-3}$ torr, sealed in the tube under vacuum and then heated to 800° C. for 24 hours. The resulting solids were isolated after cooling and breaking the tube open, ground to a powder, and resubjected to the same high temperature sintering procedure, at 800° to 1000° C. for an additional 24 hours. Powder X-ray diffraction analysis was then conducted to ensure that the sintered material was isostructural with pure standard sample of $Fe_3O_4$. The catalyst powder was then pelletized and sintered in a sealed tube as described above under vacuum at 1000° C. for several hours. The sintered pellets were then crushed, sieved and the resulting pellets impregnated with aqueous potassium carbonate to achieve the desired potassium loading, being about 1 gram-atom percent potassium, and dried. The BET (nitrogen) surface areas measured were in the range from about 0.25 to 0.30 $m^2/g$. The results are listed below in Table I.

TABLE 1

| Composition | $Fe_{3-y}Co_yO_4/1\%K$ | |
| --- | --- | --- |
| | y | BET ($m^2/g$) |
| Control | 0.00 | 0.27 |
| A | 0.0275 | 0.30 |
| B | 0.150 | 0.29 |
| C | 0.375 | 0.25 |
| D | 0.750 | 0.28 |

The powder x-ray diffraction spectrum of each of the obtained Fe—CO spinels showed that they were a single phase and isostructural with $Fe_3O_4$. They differed from one another in slight shifts of the 2 theta reflection values without altering the overall profile.

EXAMPLE 2

Catalyst B, $Fe_{2.85}Co_{0.15}O_4/1\%K$, where Y=0.15, was prepared by the procedure described in Example 1. X-ray diffraction analysis showed this material to be isostructural with $Fe_3O_4$, although there was a slight change in the unit cell constant where the unit cell constant is about 0.01 to 0.02 Å smaller than that of $Fe_3O_4$. The sintered material was found to have a low surface area, less than 5 $m^2/g$. This material was crushed and sieved to 20–80 mesh before use in this example under F—T (Fischer-Tropsch) fixed bed reaction conditions. The reactor was charged with 8.8 cc of catalyst with a thermocouple placed at the center of the bed. The catalyst compositions of 20–80 mesh particle size, were pretreated with hydrogen gas in nitrogen (90% hydrogen/nitrogen) at 500° C., 100 sccm (680 v/v/hr.) of hydrogen gas at 100 psig for 5 to 7 hours in a fixed bed tubular vertical reactor constructed of 316 stainless steel, and being 0.51" internal diameter and 15" long. The runs were conducted using a 1:1 $H_2$/CO mixture, at 570 v/v/hr., 300 psig, at the indicated temperatures, which are furnace temperatures in this and the remaining examples unless otherwise indicated as bed temperatures. In many of the cases, the bed temperature was 10°–30° C. higher than the indicated furnace temperature, due to primarily to the limited heat removal capabilities of the reactor system and the highly exothermic nature of the reaction. The highly exothermic nature of the reaction. The overall collected products which were collected after catalyst pretreatment, and one hour on stream with CO/$H_2$, were analyzed by gas chromatography.

Representative results obtained with catalyst composition B, $Fe_{2.85}Co_{0.15}O_4/1\%K$, relative to the control (see Table I) are presented below in Table II.

TABLE II

| Catalyst | $Fe_3O_4/1\%K^a$ | $Fe_{2.85}Co_{0.15}O_4/1\%K^b$ |
| --- | --- | --- |
| Temp °C. | 305 | 270 |
| % CO Conversion | 79 | 98 |
| % CO to $CO_2$ | 36 | 42 |

TABLE II-continued

| Catalyst | $Fe_3O_4/1\%K^a$ | $Fe_{2.85}Co_{0.15}O_4/1\%K^b$ |
|---|---|---|
| % CO to HC[c] | 43 | 56 |
| Wt. % Selectivity | | |
| $CH_4$ | 8.5 | 9.1 |
| $C_2H_6$ | 2.1 | 4.3 |
| $C_2H_4$ | 6.5 | 9.8 |
| $C_3H_8$ | 1.4 | 1.9 |
| $C_3H_6$ | 10.6 | 20.3 |
| $C_4H_{10}$ | 1.7 | tr. |
| $C_4H_8$ | 9.5 | 9.3 |
| $C_5^+$ | 59.7 | 45.2 |

[a]Control.
[b]Composition B.
[c]Hydrocarbons.

As is seen from the data, Catalyst B, derived from the cobalt-containing spinel, exhibited greater activity at lower temperatures and higher $C_2$-$C_4$ olefin selectivity than the all iron control catalyst.

It should be noted that unless stated differently herein, the catalysts used in each of the following examples were in powder form of 20–80 mesh, used as is, or diluted with crushed quartz powder, totalling a catalyst volume of about 8–8.8 cc.

Further, the apparatus used was the same as described in this Example 2 and the pretreatment procedure was substantially the same as described in Example 2.

Values for selectivity weight percentages of product hydrocarbons are reported on a $CO_2$-free basis unless otherwise stated.

EXAMPLE 3

Four (4) cc. of Catalyst B, described above in Example 2, was mixed with 20–80 mesh solid quartz powder (crushed quartz tubes) in 4.0 cc quantity, and the mixture was placed into the reactor described in Example 1, and pretreated by contacting with a 9:1 $H_2/N_2$ feedstream at 500° C., 750 v/v/hr., 100 psig, for 5.5 hours.

The mixed diluted catalyst was then contacted with 1:1 $H_2/CO$ at 270° C., 300 psig, at 2000 v/v/hr. for 12 hours on stream. The product distribution was analyzed by gas chromatography, and the results are given below in Table III.

TABLE III

| Catalyst | 1:1 Catalyst B/quartz powder |
|---|---|
| % Conversion | 62 |
| % CO to $CO_2$ | 24 |
| % CO to H.C. | 38 |
| Wt. % Selectivity | |
| $CH_4$ | 9.2 |
| $C_2°$-$C_5°$ | 7.9 |
| $C_2^=$-$C_5^=$ | 48.2 |
| $C_6^+$ | 34.7 |

As is seen from the data, the catalyst derived from the iron-cobalt spinel provides good activity and high $C_2$-$C_5$ olefin selectivity with high $H_2/CO$ feed rates.

EXAMPLE 4

Catalyst B, in a 1:1 admixture with crushed quartz, as described in Example 3, was run under a different set of F-T synthesis conditions as described below.

Following substantially the same pretreatment, described in Example 3, about 8 cc of the catalyst in the same described apparatus as above was contacted with 1:1 $H_2/CO$, at a bed temperature of 250° to 270° C., a standard hourly space velocity (SHSV) of 1000 v/v/hr. at 300 psig, for 12 hours. The products were collected and the product distribution data were analyzed by gas chromatography. Results are given below in Table IV.

TABLE IV

| % CO conversion | 98 |
|---|---|
| % CO to $CO_2$ | 43 |
| % CO to HC | 55 |
| Wt. % Selectivity $CH_4$ | 7.2 |
| $C_2^=/C_2°$ | 2.6 |
| $C_2/C_1$ | 2.1 |
| % $C_2$-$C_6$ | 50.8 |
| % Olefins (of $C_2$-$C_6$ total) | 86 |
| $C_7^+$ | 42 |

As is seen from the data, the Fe—Co Catalyst B generates a $C_2$-$C_6$ fraction which is olefin rich even at high conversion conditions.

EXAMPLE 5

Catalyst B and the control, prepared by the procedure described in Example 1, were pretreated by the procedure described in Example 3 in the apparatus described in Example 2.

Each catalyst in 8 cc volume, after pretreatment, was contacted with 1:1 $H_2/CO$ at 300 psig pressure, 1000 v/v/hr. (SHSV) for 12 hour run times at the temperatures listed below in Table VI, in same apparatus described in Example 2. Product samples were collected and analyzed after 12 hours onstream with $CO/H_2$.

TABLE VI

| | Catalyst B | Control | Control |
|---|---|---|---|
| % CO Conversion | 98 | 67 | 87 |
| % CO to $CO_2$ | 40 | 31 | 37 |
| % CO to HC | 58 | 36 | 50 |
| Temp. °C. | 270 | 305 | 340 |
| $C_2:C_1$ | 2.2 | 1.2 | 0.7 |
| % $C_2$-$C_6$ | 62 | 41 | 53 |
| % Olefin (of $C_2$-$C_6$ total) | 89 | 88 | 70 |
| Weight % Selectivity | | | |
| $C_1$ | 7.4 | 5.8 | 19.0 |
| $C_2°$ | 4.4 | 1.3 | 7.8 |
| $C_2^=$ | 11.6 | 5.4 | 5.7 |
| $C_3°$ | 1.5 | 1.0 | 2.6 |
| $C_3^=$ | 20.0 | 9.4 | 15.9 |
| $C_4°$ | tr. | 1.4 | 2.0 |
| $C_4^=$ | 11.3 | 8.8 | 8.6 |
| $C_5°$ | 0.3 | 1.0 | 1.1 |
| $C_5^=$ | 7.4 | 7.0 | 4.0 |
| $C_6°$ | 0.8 | 0.3 | 2.6 |
| $C_6^=$ | 4.6 | 5.0 | 3.0 |
| $C_7^+$ | 30.7 | 53.6 | 27.7 |

As is seen from the data, the catalyst derived from the cobalt containing spinel provided greater activity, i.e. 98% CO conversion, than the all-iron oxide control catalysts even though they were operated at 35° C. and 70° C. higher temperatures. The Fe—Co catalyst generated more $C_2$-$C_6$ olefins than either of the control catalysts and substantially less methane than the control catalyst at high conversion (about 87%) conditions.

EXAMPLE 7

CATALYST PREPARATION

Following the general procedure described in Example 1 the following catalysts were prepared having the empirical formula: $Fe_{3-y}Co_yO_4/1\%K$: where y=0.03, 0.15, 0.375 and 0.75, respectively. The surface areas of the obtained materials were in the range of 0.1 to 0.5 $m^2g$.

The above-prepared catalysts were pretreated by the procedure described in Example 2 and in the apparatus described in Example 4, and subjected to hydrocarbon synthesis under the following reaction conditions:

| | |
|---|---|
| Temperature = | 295 ± 10° C. |
| Pressure = | 300 psig |
| Space Velocity = | 1000 v/v/hr. |
| $H_2/CO$ ratio = | 1:1 |
| Run Time = | 12 hours |
| Catalyst = | 8 cc volume, 20-80 mesh size |

Analysis of products were performed after 12 hours of run time. Results are shown in Table VII below.

TABLE VII

Performance of $Fe_{3-y}Co_yO_4/1\%K$

| Y = | 0.03 | 0.15 | 0.375 | 0.80 |
|---|---|---|---|---|
| % CO Conversion | 97 | 98 | 97 | 98 |
| To $CO_2$ | 27 | 40 | 41 | 42 |
| To HC's | 70 | 58 | 56 | 56 |
| Wt. % Selectivity | | | | |
| $CH_4$ | 8.3 | 7.4 | 18.0 | 13.2 |
| $C_2^=-C_6^=$ | 46.5 | 53.1 | 41.4 | 53.0 |
| $C_2°-C_6°$ | 6.9 | 7.2 | 13.3 | 10.6 |
| $C_7^+$ | 38.3 | 32.3 | 27.3 | 23.2 |

The results show the importance of maintaining the Fe:Co atomic ratio within the preferred range i.e. y=0.03 to y=0.40 at the specific conditions in this Example, excessive levels of $CH_4$ are generated at high cobalt levels, i.e., y=0.375 where Fe:Co=7:1.

EXAMPLE 8

This example shows the performance of Catalyst C, $Fe_{2.625}Co_{0.375}O_4$ in hydrocarbon synthesis at different temperatures.

The catalyst was pretreated according to the procedure described in Example 2 and in the same described apparatus. The hydrocarbon synthesis runs were conducted at the indicated temperatures using 8 cc. volume of catalyst being undiluted with quartz and 20-80 mesh particle size at 1:1 $H_2/CO$, 1000 v/v/hr. (SHSV), 300 psig for 1-12 hours onstream.

TABLE VII

Performance of $Fe_{2.625}Co_{0.375}O_4/1\%K$

| Furnace Temp °C. | 225 | 240 | 260 | 270 | 280 | 290 |
|---|---|---|---|---|---|---|
| Bed Temp °C. | 230 | 248 | 304 | 325 | 331 | 340 |
| % CO Conversion | 30 | 31 | 97 | 98 | 98 | 98 |
| To $CO_2$ | 4 | 7 | 40 | 33 | 41 | 41 |
| To HC's | 26 | 24 | 57 | 55 | 57 | 57 |
| Wt. % Selectivity - $CO_2$—free basis | | | | | | |
| $CH_4$ | 8.1 | 8.2 | 19.1 | 16.7 | 18.3 | 19.1 |
| $C_2^=-C_5^=$ | 42.3 | 55.3 | 37.1 | 31.9 | 37.8 | 24.8 |
| $C_2°-C_5°$ | 14.4 | 22.0 | 17.7 | 10.6 | 13.2 | 14.8 |
| $C_6^+$ | 35.2 | 34.5 | 26.1 | 40.8 | 30.7 | 41.3 |

As seen from the data, the change in $CH_4$ selectivity as a function of temperature-conversion indicates that catalysts which contain relatively high levels of cobalt, i.e. an iron/cobalt atomic ratio of 7.0, while useful should be operated at lower temperature-conversion conditions to achieve low $CH_4$ productivity. As further seen in the data, good $C_2-C_6$ olefin selectivity is achieved over the entire operating range. The system provided optimal performance in runs where the bed temperature was lower than 304° C.

EXAMPLE 9

This example shows the improved performance of Catalyst C, $Fe_{2.625}Co_{0.375}O_4$, at low (150 psig) pressure relative to (300 psig) high pressure conditions. The catalyst was prepared by the procedure outlined in Example 1, and subjected to the pretreatment and operating procedures substantially as described in Examples 2 and 4, respectively.

The results in Table VIII below show that even at relatively high cobalt levels, i.e. Fe:Co of 7.0, good olefin selectivity and high conversion can be achieved at lower pressures, i.e. 150 psig.

TABLE VIII

Performance of $Fe_{2.625}Co_{0.375}O_4/1\%K$ at 150 and 300 psig

| Pressure (psig) | 150 | 300 |
|---|---|---|
| % CO Conversion | 92 | 97 |
| % To $CO_2$ | 38 | 41 |
| % To HC | 54 | 56 |
| Wt. % Selectivity ($CO_2$—free basis) | | |
| $CH_4$ | 7.2 | 17.9 |
| $C_2^=-C_5^=$ | 53.4 | 38.1 |
| $C_2°-C_5°$ | 4.5 | 12.7 |
| $C_6^+$ | 34.9 | 31.3 |

EXAMPLE 10

This example shows the effect of $H_2$ treatment at 350° C. to reduce $CH_4$ selectivity of an "aged catalyst", in this case Catalyst B, which had been onstream for 72 hours. It is believed that the treatment with $H_2$ at 350° C. for 5 hrs. at 100 psig, 750 SHSV, removes a carbonaceous surface layer which develops on the catalyst during extended operating periods. The procedures described in Example 1 were used to prepare the catalyst while the procedure of Example 3 were used to pretreat, and operate this catalyst under the hydrocarbon synthesis conditions of 270° C., 0.66:1 $H_2/CO$, 2000 v/v/hr. (SHSV), 300 psig, 50% catalyst dilution with quartz powder in 8 cc total volume, catalyst particle size of 20-80 mesh.

TABLE IX $H_2$ Treatment Improves Time Dependent Performance of $Fe_{2.85}Co_{0.15}O_4/1\%K$

| Hours on stream | 72[a] | 96[b] |
|---|---|---|
| % CO Conversion | 48 | 62 |
| % CO to $CO_2$ | 23 | 28 |
| % CO to HC | 25 | 34 |
| Wt. % Selectivity ($CO_2$—free basis) | | |
| $CH_4$ | 12.0 | 7.9 |
| $C_2^=-C_5^=$ | 43.3 | 46.3 |
| $C_2°-C_5°$ | 7.1 | 6.6 |
| $C_6^+$ | 37.6 | 40.1 |

[a]Prior to hydrogen rejuvenation.
[b]After 72 hours onstream, $H_2$ treatment described above, then additional 24 hours onstream with $CO/H_2$.

EXAMPLE 11

This example demonstrates the performance of Catalyst B, $Fe_{2.85}Co_{0.15}O_4$, at various temperatures under hydrocarbon synthesis conditions. The catalyst was 50% diluted with quartz powder as described in the previous Example. The respective procedures outlined in Examples 1 and 3 were used to prepare, pretreat and operate this catalyst under the hydrocarbon synthesis conditions listed below in Table X.

TABLE X

| | $Fe_{2.85}Co_{.15}O_4/1\%K$ Performance | | |
|---|---|---|---|
| Run | 1 | 2 | 3 |
| Temp °C. | 230 | 250 | 270 |
| Pressure (psig) | 300 | 300 | 300 |
| $H_2/CO$ | 1.0 | 1.0 | 1.0 |
| SHSV | 1800 | 1800 | 1800 |
| % CO Conv. | 36.4 | 97.5 | 98.4 |
| HR on Stream | 2 | 4 | 6 |
| % CO to $CO_2$ | 14 | 44.0 | 43.0 |
| % CO to HC | 22.4 | 53.5 | 55.4 |
| Wt. % Selectivity ($CO_2$—free basis) | | | |
| $CO_2$ | 37.9 | 45.0 | 43.8 |
| $CH_4$ | 1.3 (2.1) | 2.6 (4.7) | 3.2 (5.7) |
| $C_2^=$ | 2.0 (3.22) | 3.0 (5.5) | 3.4 (6.0) |
| $C_2^°$ | 0.4 (0.6) | 0.8 (1.5) | 0.8 (1.4) |
| $C_3^=$ | 4.1 (6.6) | 5.4 (9.8) | 6.3 (11.2) |
| $C_3^°$ | 0.8 (1.3) | 0.6 (1.1) | 0.6 (1.1) |
| $C_4^=$ | 1.7 (2.7) | 3.4 (6.2) | 4.0 (7.1) |
| $C_4^°$ | 0.1 (0.2) | 0.5 (0.9) | 0.5 (0.9) |
| $C_5^=$ | 1.4 (2.3) | 2.6 (4.7) | 3.5 (6.2) |
| $C_5^°$ | 0.3 (0.5) | 0.5 (0.9) | 0.9 (1.6) |
| $C_6^=$ | 1.2 (1.9) | 1.9 (3.5) | 2.2 (3.9) |
| $C_6^°$ | 0.4 (0.6) | 0.3 (0.5) | 0.3 (0.5) |
| $C_7^+$ | 48.4 (78.0) | 33.4 (60.7) | 30.5 (54.4) |

EXAMPLE 12

This example demonstrates the performance of Catalyst B, $Fe_{2.85}Co_{0.15}O_4$ at various temperatures in the form of undiluted catalyst. The catalyst was prepared by the procedure described in Example 1 and pretreated and operated as respectively described in Examples 2 and 4. The process conditions for each run are listed below in Table XI. In contrast to Run 4 shown below, bed dilution as employed in Example 10 allows the system to operate under more isothermal conditions thereby minimizing the extent of carbon and carbonaceous deposit formation.

TABLE XI

| | $Fe_{2.85}Co_{.15}O_4/1\%K$ Performance Undiluted Bed | | | |
|---|---|---|---|---|
| Run | 1 | 2 | 3 | 4 |
| SHSV: | 1000 | 1000 | 570 | 570 |
| Temp. | 235 | 270 | 235 | 270 |
| $H_2:CO$ | 1.0 | 1.0 | 1.0 | 1.0 |
| Press | 300 | 300 | 300 | 300 |
| Time on stream hr. | 8 | 10 | 16 | 18 |
| % CO Conv. | 29.4 | 98.0 | 49.1 | 98.0* |
| % CO to $CO_2$ | 8.0 | 42.0 | 22.0 | 40.0 |
| % CO to HC | 21.4 | 56.0 | 27.1 | 58.0 |
| Wt. % Select. ($CO_2$—free basis) | | | | |
| $CO_2$ | 26.2 | 42.5 | 43.5 | 40.2 |
| $CH_4$ | 1.9 | 3.0 | 1.7 | 3.7 |
| | (2.6) | (5.2) | (2.0) | (6.2) |
| $C_2^=$ | 4.3 | 4.5 | 2.5 | 4.0 |
| | (5.8) | (7.8) | (4.4) | (6.7) |
| $C_2^°$ | 1.4 | 1.7 | 0.9 | 1.7 |
| | (1.9) | (2.9) | (1.6) | (2.8) |
| $C_3^=$ | 6.4 | 7.8 | 6.6 | 8.3 |
| | (8.7) | (13.4) | (11.6) | (13.8) |
| $C_3^°$ | 0.6 | 0.6 | 0.7 | 0.8 |
| | (0.8) | (1.0) | (1.2) | (1.3) |
| $C_4^=$ | 1.4 | 4.4 | 2.5 | 3.8 |
| | (1.9) | (7.6) | (4.4) | (6.3) |
| $C_4^°$ | tr. | 0.2 | 0.4 | 3.5 |
| | (tr.) | (0.3) | (0.7) | (0.8) |
| $C_5^=$ | 0.9 | 2.8 | 1.7 | 2.7 |
| | (1.2) | (4.8) | (2.9) | (4.5) |
| $C_5^°$ | tr. | 0.1 | 0.4 | 0.35 |
| | (tr.) | (0.2) | (0.7) | (0.8) |
| $C_6^+$ | 56.9 | 32.4 | 39.1 | 34.2 |

TABLE XI-continued

| | $Fe_{2.85}Co_{.15}O_4/1\%K$ Performance Undiluted Bed | | | |
|---|---|---|---|---|
| Run | 1 | 2 | 3 | 4 |
| | (76.8) | (55.9) | (68.6) | (57.0) |

*Note: Bed plugging with wax and carbonaceous deposits limited continuous operating periods to $\leq 40$-50 hrs.

What is claimed is:

1. A hydrocarbon synthesis catalyst composition comprising an unsupported, Group IA or IIA metal salt promoted iron-cobalt single phase spinel, said spinel having the initial empirical formula:

$$Fe_xCo_yO_4$$

wherein x and y are integer or decimal values, other than zero, with the proviso that the sum of $x+y$ is 3 and the ratio of x/y is 7:1 or above, said spinel exhibiting a powder X-ray diffraction pattern substantially isostructural with $Fe_3O_4$ and said spinel having an initial BET surface area of up to about 5 $m^2/g$.

2. The composition of claim 1 wherein said ratio of x/y is 7:1 to 35:1.

3. The composition of claim 2 wherein the ratio of x/y is 19-20:1.

4. The composition of claim 2 wherein said spinel is of the formula: $Fe_{2.85}Co_{0.15}O_4$, $Fe_{2.625}Co_{0.375}O_4$, $Fe_{2.97}Co_{0.03}O_4$.

5. The composition of claim 1 further comprising a mixture of said iron-cobalt spinels, of different iron-cobalt atomic ratios, and being in admixture therewith.

6. The composition of claim 1 being further in admixture with a diluent in about a 1:4 to 9:1 diluent/catalyst composition weight ratio.

7. The composition of claim 6 wherein said diluent is selected from powdered quartz, porous silica, silicon carbide, kieselguhr, talc, powdered borosilicate glass, $TiO_2$, $SiO_2$, clays, $Al_2O_3$, zeolites, MgO, $La_2O_3$, $CeO_2$, $Cr_2O_3$ and $MnO_2$.

8. The composition of claim 1 wherein said alkali metal or alkaline earth metal salt promoter agent present in about 0.1 to 10 gram-atom % as the metal ion of the total gram-atoms metals content.

9. The composition of claim 8 wherein said promoter is selected from bicarbonates, carbonates, organic acid salts and inorganic acid salts of Group IA and IIA metals.

10. The composition of claim 9 wherein said promoter agent is potassium carbonate.

11. The composition of claim 10 being further substantially carbided by contact with a CO/hydrogen atmosphere at elevated temperature.

12. The composition of claim 1 being of the formula: $Fe_{2.85}Co_{0.15}O_4$, and containing about 1 gram-atom percent potassium.

13. A process for producing the spinel portion of the composition of claim 1 comprising heating a mixture of iron and cobalt as their oxides and/or free metals, at elevated temperature in an oxygen-free or inert atmosphere for a sufficient time until the resulting oxide mixture exhibits an X-ray diffraction pattern isostructural with $Fe_3O_4$.

14. The composition of claim 9 wherein the inorganic acid salts of Group IA and Group IIA metals are selected from the group consisting of nitrates, sulfates and halides.

15. A hydrocarbon synthesis catalyst composition comprising an unsupported, Group IA or IIA metal hydroxide promoted iron-cobalt single phase spinel, said spinel having the initial empirical formula:

$$Fe_xCo_yO_4$$

wherein x and y are integer or decimal values, other than zero, with the proviso that the sum of $x+y$ is 3 and the ratio of x/y is 7:1 or above, said spinel exhibiting a powder x-ray diffraction pattern substantially isostructural with $Fe_3O_4$ and said spinel having an initial BET surface area of up to about 5 $m^2/g$.

16. The composition of claim 15 wherein said ratio of x/y is 7:1 to 35:1.

17. The composition of claim 16 wherein the ratio of x/y is about 19-20:1.

18. The composition of claim 16 wherein said spinel is of the formula: $Fe_{2.85}Co_{0.15}O_4$, $Fe_{2.625}Co_{0.375}O_4$, $Fe_{2.97}Co_{0.03}O_4$.

19. The composition of claim 15 further comprising a mixture of said iron-cobalt spinels, of different iron-cobalt atomic ratios, and being in admixture therewith.

* * * * *